(12) United States Patent
Lu et al.

(10) Patent No.: US 9,867,769 B2
(45) Date of Patent: Jan. 16, 2018

(54) VISCOSITY BUILDING COMPOSITION FOR PERSONAL CARE PRODUCTS

(71) Applicant: Arch Personal Care Products, LP, Allendale, NJ (US)

(72) Inventors: Guojin Lu, Allendale, NJ (US); Khat Kevin Lou, Allendale, NJ (US); Joseph LiBrizzi, Hillsborough, NJ (US); Mark Garrison, Allendale, NJ (US)

(73) Assignee: Arch Personal Care Products, LP, Allendale, NJ (US)

( * ) Notice: Subject to any disclaimer, the term of this patent is extended or adjusted under 35 U.S.C. 154(b) by 0 days.

(21) Appl. No.: 15/076,853

(22) Filed: Mar. 22, 2016

(65) Prior Publication Data

US 2016/0279050 A1 Sep. 29, 2016

Related U.S. Application Data (60) Provisional application No. 62/209,667, filed on Aug. 25, 2015, provisional application No. 62/139,089, filed on Mar. 27, 2015.

(51) Int. Cl.

| | |
|---|---|
| *A61K 8/86* | (2006.01) |
| *A61K 8/85* | (2006.01) |
| *A61K 31/58* | (2006.01) |
| *A61Q 5/02* | (2006.01) |
| *A61Q 19/10* | (2006.01) |
| *A61K 8/34* | (2006.01) |
| *A61K 8/58* | (2006.01) |
| *A61Q 19/00* | (2006.01) |

(52) U.S. Cl.
CPC ............... *A61K 8/86* (2013.01); *A61K 8/342* (2013.01); *A61K 8/58* (2013.01); *A61K 8/85* (2013.01); *A61Q 5/02* (2013.01); *A61Q 19/00* (2013.01); *A61Q 19/10* (2013.01); *A61K 2800/48* (2013.01)

(58) Field of Classification Search
CPC ... A61K 8/86; A61K 8/58; A61K 8/85; A61K 8/34; A61Q 19/10; A61Q 5/02
See application file for complete search history.

(56) References Cited

U.S. PATENT DOCUMENTS

| | | | |
|---|---|---|---|
| 5,244,664 | A | 9/1993 | Godtfredsen |
| 5,466,719 | A | 11/1995 | Jakobson et al. |
| 6,534,069 | B1 | 3/2003 | Asmus et al. |
| 8,466,100 | B2 | 6/2013 | Ponder et al. |
| 2007/0128147 | A1 | 6/2007 | Schwartz et al. |
| 2007/0190132 | A1 | 8/2007 | Andrysek et al. |
| 2008/0044497 | A1* | 2/2008 | Sussan ............... A61K 31/21 424/725 |
| 2010/0215598 | A1* | 8/2010 | Poletti ................ A61K 8/39 424/59 |
| 2015/0313823 | A1 | 11/2015 | Lockett et al. |

FOREIGN PATENT DOCUMENTS

| | | |
|---|---|---|
| DE | 4330597 | 3/1995 |
| EP | 0569028 | 11/1993 |
| EP | 2314272 | 4/2011 |
| EP | 1334717 | 8/2013 |
| JP | H072677 | 1/1995 |
| WO | WO 2014/100709 | 6/2014 |

OTHER PUBLICATIONS

Trüeb (JDDG vol. 5 (2007) (Band5).*
International Search Report and Written Opinion for PCT/US2016/023538, dated Jun. 8, 2016, 10 pages.

* cited by examiner

*Primary Examiner* — Shirley V Gembeh
(74) *Attorney, Agent, or Firm* — Dority Manning, P.A.

(57) ABSTRACT

A viscosity building composition is described. The viscosity building composition comprises a fatty alcohol in combination with one or more polyglyceryl esters. In one embodiment, the composition contains a fatty alcohol in combination with a polyglyceryl monoester. In an alternative embodiment, the composition contains a fatty alcohol combined with a polyglyceryl polyester, such as a polyglyceryl diester or a polyglyceryl triester. In still another embodiment, the composition comprises a fatty alcohol mixed with a blend of polyglyceryl esters. The blend may include at least one polyglyceryl monoester in combination with at least one polyglyceryl polyester, such as a diester, triester, tetraester or decaester. The polyglyceryl polyester is present generally in an amount greater than the monoester. In an alternative embodiment, the blend may include two or more polyglyceryl polyesters. The blend of polyglyceryl esters has been found to dramatically enhance the ability of the fatty alcohol to increase viscosity and build body in personal care products.

11 Claims, 4 Drawing Sheets

VISCOSITY BUILDING COMPOSITION FOR PERSONAL CARE PRODUCTS

RELATED APPLICATIONS

The present application is based on and claims priority to U.S. Provisional Patent application Ser. No. 62/209,667, filed on Aug. 25, 2015, and U.S. Provisional Patent application Ser. No. 62/139,089, filed on Mar. 27, 2015, both of which are incorporated herein by reference.

BACKGROUND

Many different personal care products exist in the marketplace. Such personal care products include shampoos, conditioners, cosmetic products, hand moisturizers, body creams, shower gels and other detergents, and the like. Most of these products are for application to a certain area of the body. To be marketable, these products must meet certain stringent requirements in addition to being well suited for their intended use. For instance, many of these products must have a pleasing fragrance or no fragrance, must have a uniform consistency, and must apply evenly to a surface with a controlled viscosity. Typically, thicker personal care products are described as luxurious and therefore are more desired.

Many personal care products comprise emulsions. The products contain emulsifiers to stabilize the emulsion droplets, thickeners to add body, emollients to seal in moisture, and humectants to bind water. To improve the thickness and increase the viscosity of an emulsion system, fatty alcohols are typically added to the products at a level sufficient to yield an emulsion with good body. Problems, however, are experienced in increasing the body or viscosity of the emulsion to desired levels without having deleterious effects on the overall product.

For instance, in order to build the viscosity of an emulsion system, increased levels of a fatty alcohol or increased levels of various polymers may be added to the emulsion. Adding higher levels of these components, however, not only leads to significantly higher costs of the goods, but such increased levels may adversely impact on the aesthetics of the formula. For instance, addition of polyacrylates will build emulsion viscosity but may lead to increased tackiness of the emulsion. In other embodiments, increased thickeners may adversely affect the color of the product and/or adversely affect the smell of the product.

In view of the above, those skilled in the art have attempted to develop better thickeners or viscosity building compositions that can be added in minimal amounts for increasing the viscosity of the products to desired levels. In this regard, the present disclosure is directed to improved viscosity building compositions.

SUMMARY

In general, the present disclosure is directed to viscosity building compositions that may be used in various and diverse applications. In one embodiment, the viscosity building composition of the present disclosure can be added to a personal care product for increasing the viscosity and enhancing the body of the product. In general, the present disclosure is directed to certain combinations of polyglyceryl esters that have been found to have a synergistic viscosity building effect with fatty alcohols yielding emulsions with unexpectedly improved body or viscosity at lower than expected levels of fatty alcohol.

For instance, in one embodiment, the present disclosure is directed to a viscosity building composition comprising a fatty alcohol in combination with at least one polyglyceryl ester. For instance, the composition can comprise a fatty alcohol in combination with a polyglyceryl monoester. In an alternative embodiment, the composition may comprise a fatty alcohol in combination with a polyglyceryl polyester. In still another embodiment, the composition may comprise a fatty alcohol in combination with a blend of polyglyceryl monoesters, a blend of polyglyceryl polyesters, or a blend containing both a polyglyceryl monoester and at least one polyglyceryl polyester.

In one embodiment, for example, the viscosity building composition comprises a fatty alcohol in combination with at least two polyglyceryl esters, such as a first polyglyceryl ester and at least a second polyglyceryl ester. The first polyglyceryl ester may comprise a polyglyceryl monoester of a carboxylic acid, such as a fatty acid. The second polyglyceryl ester, on the other hand, may comprise a polyglyceryl polyester, such as a di-, tri-, tetra-, penta-, or decaester of a carboxylic acid, such as a fatty acid. In one embodiment, the first and second polyglyceryl esters both comprise polyglycerol polyesters alone or in combination with one or more polyglyceryl monoesters.

When the viscosity building composition contains a mixture of a first polyglyceryl ester and a second polyglyceryl ester as described above, the weight ratio of the first polyglyceryl ester to the second polyglyceryl ester in the composition is from about 1:100 to about 100:1, such as from about 1:50 to 95:5. In one embodiment, the composition may contain greater amounts of the second polyglyceryl ester in comparison to the first polyglyceryl ester. For instance, the weight ratio of the first polyglyceryl ester to the second polyglyceryl ester can be from about 1:50 to about 1:1, such as from about 1:35 to about 2:3, such as from about 1:25 to about 1:3.

In one embodiment, the polyglyceryl esters, such as the first polyglyceryl ester and the second polyglyceryl ester, are formed from saturated fatty acids as opposed to unsaturated fatty acids. For instance, saturated fatty acids include caprylic acid, capric acid, lauric acid, myristic acid, palmitic acid, stearic acid, arachidic acid, behenic acid, lignoceric acid, and cerotic acid.

The fatty alcohol present in the composition may comprise, for instance, any suitable fatty alcohol having a carbon chain length of from about 4 carbon atoms to about 36 carbon atoms, such as from about 6 carbon atoms to about 28 carbon atoms. In one embodiment, the fatty alcohol may comprise a mixture of fatty alcohols. Examples of fatty alcohols include cetyl alcohol, stearyl alcohol, lauryl alcohol, myristyl alcohol, behenyl alcohol, and mixtures thereof. In one embodiment, the weight ratio of the fatty alcohol to the one or more polyglyceryl esters in the composition is from about 1:10 to about 10:1, such as from about 1:5 to about 10:1, such as from about 1:1 to about 5:1, especially when the composition contains a first polyglyceryl ester and a second polyglyceryl ester as described above.

When the composition of the present disclosure comprises a fatty alcohol in combination with a single polyglyceryl ester, the weight ratios may vary from the above. For instance, when the composition contains a fatty alcohol in combination with only one of a polyglyceryl monoester or a polyglyceryl polyester, the weight ratio of the fatty alcohol to the polyglyceryl ester in the composition can be from about 2:1 to about 1:10, such as from about 1:1 to about 1:5, such as from about 1:1.5 to about 1:3.

The polyglyceryl esters present in the composition can generally contain from about 2 molecules to about 12 molecules of glycerin (based on an average). In one embodiment, the second polyglyceryl ester comprises a diester. For instance, the polyglyceryl ester may comprise a polyglyceryl distearate. The first polyglyceryl ester, on the other hand, may comprise polyglyceryl monostearate, polyglyceryl monodecaoleate, polyglyceryl monooleate, or mixtures thereof.

In one embodiment, the present disclosure is directed to an emulsion containing the viscosity building composition as described above.

The viscosity building composition of the present disclosure is well suited for use in all different types of personal care products. For instance, the viscosity building composition can be incorporated into shampoos, body washes, conditioners, cosmetic products, skin creams, medications, facial cleansers, skin cleansers, hand creams, sunscreen lotions, makeup removers, body lotions, and the like. In one embodiment, the personal care product contains an emollient, a humectant, and at least one surfactant.

When the viscosity building composition is incorporated into a personal care product, the personal care product may contain one or more fatty alcohols in an amount less than about 5% by weight, such as in an amount less than about 4% by weight, such as in an amount less than about 3% by weight, such as in an amount less than about 2% by weight, such as in an amount less than about 1% by weight. The personal care product may contain the polyglyceryl esters in an amount greater than about 0.5% by weight, such as in an amount greater than about 0.75% by weight, such as in an amount greater than about 1% by weight, such as in an amount greater than about 1.25% by weight, such as in an amount greater than about 1.5% by weight, such as in an amount greater than about 2% by weight. The personal care product can contain the polyglyceryl esters generally in an amount less than about 10% by weight, such as in an amount less than about 8% by weight, such as in an amount less than about 6% by weight, such as in an amount less than about 4% by weight.

In one particular embodiment, the personal care product comprises a shampoo or body wash. The shampoo may comprise a shampoo for treating dandruff. In this regard, the shampoo or body wash may contain pyrithione.

In addition to pyrithione, the viscosity building composition of the present disclosure may also be used in conjunction with numerous different other actives or benefit agents as will be described in greater detail below.

In an alternative embodiment, the personal care product may comprise a cosmetic product. In one embodiment, the personal care product may contain both an anionic surfactant and a zwitterionic surfactant.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a viscosity building composition that can be incorporated into numerous and diverse products for increasing the viscosity of the product and/or enhancing body. For instance, the composition can be incorporated into all different types of personal care products. Such products include shampoos, body washes, conditioners, body cleansers, hand cleansers, facial cleansers, moisturizers, body creams, hand creams, makeup removers, cosmetic products, sunscreen lotions, ointments, medicaments, and the like.

In general, the viscosity building composition of the present disclosure comprises a fatty alcohol in combination with at least one type of a polyglyceryl ester. For example, in one embodiment, the viscosity building composition comprises a fatty alcohol blended with one or more polyglyceryl monoesters. In a second embodiment, the viscosity building composition comprises a fatty alcohol blended with one or more polyglyceryl polyesters. In the above embodiments, the viscosity building composition may contain no other polyglyceryl esters and may, for instance, consist of the fatty alcohol combined with one or more polyglyceryl monoesters or may consist of the fatty alcohol combined with one or more polyglyceryl polyesters. When only a single type of polyglyceryl ester is present in the composition, the amount of fatty alcohol present in the final product, such as the personal care product, can be effectively minimized while providing the desired viscosity and feel.

In an alternative embodiment of the present disclosure, the viscosity building composition comprises a fatty alcohol in combination with a mixture of polyglyceryl esters, wherein the mixture includes at least two different types of polyglyceryl esters. For instance, the viscosity building composition can include at least one polyglyceryl ester of a first type combined with at least one polyglyceryl ester of a second type.

The first polyglyceryl ester may comprise a polyglyceryl monoester. The second polyglyceryl ester, on the other hand, may comprise a polyglyceryl polyester. As used herein, a polyglyceryl polyester comprises a polyglyceryl ester that contains more than one ester. For instance, the polyglyceryl polyester may comprise a polyglyceryl diester, a polyglyceryl triester, a polyglyceryl tetraester, a polyglyceryl pentaester, a polyglyceryl decaester or mixtures thereof. For some applications, the second polyglyceryl ester is present in amounts greater than the first polyglyceryl ester or polyglyceryl monoester. In an alternative embodiment, the first polyglyceryl ester may be present in amounts greater than the second polyglyceryl ester. The present inventors discovered that the polyglyceryl esters combined with the fatty alcohol result in a synergistic and unexpected way to dramatically increase viscosity and build body.

Of particular advantage, the fatty alcohol and the one or more polyglyceryl esters are extremely safe and mild when incorporated into personal care products. The components are produced, for instance, from safe and renewable resources. In addition to viscosity building, the composition of the present disclosure also provides various other property advantages to personal care products. For instance, the composition of the present disclosure can provide a pearlescence effect to products containing the composition. The viscosity building composition is also a formulation stabilizer and has mild conditioning properties. In addition, the composition of the present disclosure is well suited to maintaining other components in a homogeneous state. For instance, the composition is particularly well suited for use with pyrithione, such as in anti-dandruff shampoos and body washes.

As described above, the viscosity building composition of the present disclosure comprises a mixture of at least one polyglyceryl ester combined with one or more fatty alcohols. Polyglyceryl esters may be represented by the following general formula:

$R^5OCH_2$—$CH(OR^4)$—$CH_2$—$(O$—$CH_2CH(OR^3)$—$CH_2)n$-$O$—$CH_2$—$CH(OR^2)$—$CH_2OR^1$, wherein R is hydrogen or an acyl group (R—CO—) of a fatty acid moiety having from 4 to 36 carbon atoms, the number of R groups is from 1 to 14, such as from 1 to 12, and n is from 2 to 14, e.g. from 3 to 10.

The backbone is generally prepared by a condensation reaction which gives a normal distribution pattern in the final polymer. The average number of glycerin units in the base polyol can total n+2. Generally, the polyglyceryls used in the formulations have a molecular weight of from 300 to 1000, such as from 500 to 800.

The fatty acid used to prepare the polyglyceryl esters can be selected from a broad range of structural types such as straight chain or branched and saturated or unsaturated. In some cases, the fatty acid chain length distribution will be a specific blend or will match that found in natural oils such as, for example, almond or sunflower oils. The preferred fatty acids have from 6 to 26 carbon atoms.

Polyglyceryl esters may be considered non-ionic surfactants and are capable of stabilizing emulsions, foams and dispersions. Polyglyceryl esters are biodegradable, biocompatible, and considered extremely safe for use.

In accordance with one embodiment of the present disclosure, the viscosity building composition contains one or more fatty alcohols in combination with only a single polyglyceryl ester or a single type of polyglyceryl ester. For instance, the composition may contain a fatty alcohol combined only with one or more polyglyceryl monoesters. Alternatively, the composition may contain a fatty alcohol in combination with only one or more polyglyceryl polyesters such as only one or more polyglyceryl diesters, only one or more polyglyceryl triesters, or only one or more polyglyceryl tetraesters, etc. The composition may contain a single fatty alcohol or a mixture of fatty alcohols. When a fatty alcohol is combined with only a single polyglyceryl ester or single type of polyglyceryl ester, the amount of fatty alcohol present in the resulting product can be minimized.

In one embodiment, the viscosity building composition contains one or more fatty alcohols in combination with a blend of polyglyceryl polyesters. In one embodiment, for instance, the blend may contain at least one polyglyceryl diester in combination with another polyglyceryl diester, a polyglyceryl triester, or a polyglyceryl tetraester. For instance, in one embodiment, the blend may contain two different polyglyceryl diesters.

In one particular embodiment, for instance, the viscosity building composition contains a polyglyceryl dipalmitate in combination with a polyglyceryl distearate. The polyglyceryl dipalmitate may contain from about 4 to about 15, such as from about 8 to about 12 polyglyceryl molecules per compound. The polyglyceryl distearate, on the other hand, may contain from about 2 to about 10, such as from about 4 to about 8 polyglyceryl molecules per compound. In one embodiment, the polyglyceryl dipalmitate can be present in relation to the polyglyceryl distearate at a weight ratio of from about 2:1 to about 1:40, such as from about 1:1 to about 1:30, such as from about 1:2 to about 1:25. In one embodiment, for instance, the polyglyceryl dipalmitate may be present in an amount less than the polyglyceryl distearate. In general, the blend of polyglyceryl polyesters may be formulated so as to have an HLB value of from about 6 to about 7.5, such as from about 6 to about 6.5.

In an alternative embodiment, the viscosity building composition contains one or more fatty alcohols in combination with a first polyglyceryl ester and a second polyglyceryl ester. The first polyglyceryl ester may comprise a polyglyceryl monoester. The second polyglyceryl ester, on the other hand, may comprise a polyglyceryl polyester, such as a polyglyceryl diester, a polyglyceryl triester, a polyglyceryl tetraester, a polyglyceryl pentaester, a polyglyceryl decaester, or mixtures thereof. The one or more polyglyceryl polyesters may be present in an amount greater than the first polyglyceryl ester or vice versus.

Various different polyglyceryl monoesters are available that may be used in the present disclosure. Such polyglyceryl esters include, for instance, polyglyceryl monostearate. For example, the polyglyceryl monostearate may comprise polyglyceryl-10 stearate, polyglyceryl-3 stearate, or mixtures thereof. Other polyglyceryl monoesters include polyglyceryl decaoleate such as polyglyceryl-10 decaoleate, polyglyceryl oleate such as polyglyceryl-10 oleate, and mixtures thereof.

Various different polyglyceryl polyesters are also available that may be used in the present disclosure. Such polyglyceryl polyesters present in the composition may comprise a polyglyceryl diester, triester, tetraester, pentaester, decaester, and the like. In one embodiment, for instance, the composition contains a polyglyceryl diester. Examples of polyglyceryl diesters include polyglyceryl distearate, such as polyglyceryl-6 distearate, polyglyceryl dipalmitate such as polyglyceryl-10 dipalmitate, and mixtures thereof. In another embodiment, the polyglyceryl polyester may comprise a polyglyceryl decastearate and/or a polyglyceryl decaoleate, which may be used alone or in combination with another polyglyceryl polyester.

As described above, the polyglyceryl esters are formed from fatty acids. In one embodiment, the first polyglyceryl ester, the second polyglyceryl ester, or both polyglyceryl esters are formed using a saturated fatty acid. For instance, saturated fatty acids include caprylic acid, capric acid, lauric acid, myristic acid, palmitic acid, stearic acid, arachidic acid, behenic acid, lignoceric acid, and cerotic acid. Unsaturated fatty acids may also be used to produce the polyglyceryl esters. In one embodiment, however, the amount of polyglyceryl ester present in the composition made from an unsaturated fatty acid is minimized. For instance, the polyglyceryl esters contained in the composition may comprise one or more polyglyceryl esters made from an unsaturated fatty acid in an amount less than about 20% by weight, such as in an amount less than about 10% by weight, such as in an amount less than about 5% by weight.

When the viscosity building composition of the present disclosure contains a mixture of different types of polyglyceryl esters, the first polyglyceryl ester which may comprise one or more polyglyceryl monoesters and the second polyglyceryl ester which may comprise one or more polyglyceryl polyesters may be present in the viscosity building composition at a weight ratio of from about 1:100 to about 100:1, such as from about 1:50 to 95:5. The first polyglyceryl ester and the second polyglyceryl ester may also be present in the viscosity building composition at a weight ratio of from about 1:50 to about 1:1, such as from about 1:35 to about 2:3, such as from about 1:25 to about 1:3. In one particular embodiment, the weight ratio may be from about 1:10 to about 1:30, such as from about 1:15 to about 1:25.

In one embodiment, the polyglyceryl ester blend used in accordance with the present disclosure has a hydrophilic-lipophilic balance ("HLB") of about 12 or less, such as about 10 or less. The HLB can be from about 6 to about 8 or from about 8 to about 12. The HLB, as used herein, is the standard HLB according to Griffin, J. Soc. Cosm. Chem., Vol. 5, page 249 (1954).

In one embodiment, the polyglyceryl ester blend can be formulated so as to have an HLB that matches at least one other component in the product being formed. For instance, many products, such as personal care products, contain an oil phase component. The oil phase component of the product can have a particular HLB value. In one embodiment, the polyglyceryl ester blend is formulated so as to have an HLB that is within ±2, such as ±1, such as ±0.5 of the HLB of the oil phase contained in the product.

When the composition only contains a single polyglyceryl ester, the single polyglyceryl ester can be selected so as to have an HLB that matches the HLB of the oil phase contained in the product as described above.

The present inventors discovered that adding one or more fatty alcohols to a composition emulsified with one or more polyglyceryl esters as described above may yield a synergistic viscosity increase not seen when using fatty alcohols alone or conventional emulsifiers. A fatty alcohol generally refers to a straight or branched carbon chain primary alcohol that can have a carbon chain length of from about 4 carbon atoms to about 36 carbon atoms. Fatty alcohols, for instance, can be produced from vegetable oils and animal fats. Examples of fatty alcohols that may be incorporated into the composition of the present disclosure include cetyl alcohol, stearyl alcohol, lauryl alcohol, myristyl alcohol, behenyl alcohol, and the like. Such fatty alcohols have a carbon chain length of from about 12 carbon atoms to about 22 carbon atoms. In one embodiment, the fatty alcohol may comprise a mixture of fatty alcohols. For instance, the fatty alcohol may comprise cetyl stearyl alcohol. In one particular embodiment, the fatty alcohol comprises a mixture of cetyl alcohol, stearyl alcohol, myristyl alcohol, and behenyl alcohol.

The fatty alcohol can be present in the viscosity building composition in relation to the polyglyceryl esters at a weight ratio of from about 1:10 to about 10:1, such as from about 1:5 to about 10:1, such as from about 1:1 to about 5:1. In one embodiment, the weight ratio between the fatty alcohol and the polyglyceryl esters can be from about 1:2 to about 5:2. When the viscosity building composition contains a fatty alcohol in combination with only a single polyglyceryl ester, the weight ratio of the fatty alcohol to the polyglyceryl ester can be from about 2:1 to about 1:10, such as from about 1:1 to about 1:5, such as from about 1:1.5 to about 1:3.

Of particular advantage, the amount of fatty alcohol incorporated into a personal care product can be minimized due to the synergistic effects with the one or more polyglyceryl ester. For instance, once the viscosity building composition is incorporated into a personal care product, one or more fatty alcohols can be present in the product in an amount less than about 10% by weight, such as in an amount less than about 7% by weight, such as in an amount less than about 6% by weight, such as in an amount less than about 5% by weight, such as in an amount less than about 4% by weight, such as in an amount less than about 3% by weight, such as even in an amount less than about 2% by weight. One or more fatty alcohols are typically present in the personal care product in an amount greater than about 0.05% by weight, such as in an amount greater than about 0.1% by weight.

In one embodiment, the viscosity building composition contains a fatty alcohol in combination with only a single polyglyceryl ester, such as a polyglyceryl monoester or a polyglyceryl diester. In this embodiment, the fatty alcohol can be present in the personal care product in an amount less than 1% by weight, such as in an amount less than 0.8% by weight, such as in an amount less than 0.6% by weight.

The total amount of polyglyceryl esters present in the personal care product is generally less than about 10% by weight, such as in an amount less than about 8% by weight, such as in an amount less than about 6% by weight, such as in an amount less than about 4% by weight. The total amount of polyglyceryl esters are present in the personal care product generally in an amount greater than about 0.1% by weight, such as in an amount greater than about 0.5% by weight, such as in an amount greater than about 0.75% by weight, such as in an amount greater than about 1% by weight, such as in an amount greater than about 1.25% by weight, such as in an amount greater than about 1.75% by weight.

The viscosity building composition of the present disclosure as described above can be incorporated into numerous and diverse products, such as various different types of personal care products. The personal care product may contain one or more emulsifiers, one or more thickeners, one or more emollients, and/or one or more humectants. For instance, some components that may be incorporated into the personal care product include glycerin, xanthan gum, triglycerides such as caprylic triglyceride or capric triglyceride, shea butter, and one or more preservatives. Each of the above components can be present in the product in an amount from about 0.1% to about 10% by weight, such as in an amount from about 0.2% to about 8% by weight.

In one embodiment, the personal care product contains one or more surfactants. For instance, the personal care product can contain an anionic surfactant in combination with a zwitterionic surfactant.

One type of anionic surfactants is the water-soluble salts of $C_{10}$ to $C_{14}$ fatty alcohol sulfates. The sodium salts are most prevalent but other soluble salts include potassium, ammonium, diethanol- and triethanolammonium cations.

In one embodiment, sodium lauryl sulfate is used. The concentration range of the anionic surfactant on a 100% total formulation weight basis is in the range of 1% to 20%. The anionic concentration can be minimized by a high loading of zwitterionic surfactants to the extent practical.

As a general matter, anionic surfactants are exemplified by the alkali metal salts of organic sulfuric reaction products having in their molecular structure an alkyl radical containing from 8 to 22 carbon atoms and a sulfonic acid or sulfuric acid ester radical (included in the term alkyl is the alkyl portion of higher acyl radicals). Preferred alkyl sulfates are sodium coconut oil fatty acid monoglyceride sulfate and sulfonates and those obtained by sulfating higher alcohols, i.e., those containing $C_8$ to $C_{18}$ carbon atoms. Other examples are sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; and water-soluble salts of condensation products of fatty acids with sarcosine.

The zwitterionic surfactants can comprise cocamidopropyl betaine and the use level ranges from about 3 to about 25 wt. % on a 100% actives basis.

Other alkylamidopropyl betaines can be used having alkyl groups derived from $C_{10}$ to $C_{16}$ fatty acids. The corresponding alkylamidopropyl sultaines are acceptable, especially cocamidopropyl sultaine.

Additional zwitterionic surfactants which can be used are substituted imidazolines. The surfactants are described in the CTFA dictionary as sodium cocoamphoacetate and disodium cocoamphodiacetate. In addition to, or in place of, the coco-derived imidazolines, one can use similar structures prepared from $C_{10}$ to $C_{16}$ fatty acids. The active content of imidazoline surfactant, either as a single reagent or as a blend, runs from about 1.5% to about 2.5%.

Zwitterionic surfactants are exemplified by derivatives of aliphatic quaternary ammonium, phosphonium, and sulfonium compounds, in which the aliphatic radicals are straight chain or branched, and wherein one of the aliphatic substituents contains from about 8 to 18 carbon atoms and one contains an anionic water-solubilizing group, e.g., carboxyl, sulfonate, sulfate, phosphate, or phosphonate. A general formula for these compounds is:

wherein $R^2$ is an alkyl, alkenyl, or hydroxyalkyl radical of from about 8 to about 18 carbon atoms. They may contain up to about 10 ethylene oxide moieties and up to 1 glyceryl moiety. Y is a nitrogen, phosphorus, or sulfur atom; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from about 1 to about 4 carbon atoms; and Z is a carboxylate, sulfonate, sulfate, phosphonate, or phosphate group.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradecoxylphosphonio]-2-hydroxylpropane-1-phosphate;
3-[N, N-dipropyl-N-3-dodecoxy-2-hydroxypropylammonio]-propane-1-phosphonate;
3-(N,N-dimethyl-N-hexadecylammonio)propane-1-sulfonate;
3-(N, N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and 5-[N,N-di(3-hydroxypropyl)-N-hexadecylammonio]-2-hydroxypentane-1-sulfate.

Examples of other betaines useful herein include the high alkyl betaines such as:
coco dimethyl carboxymethyl betaine,
lauryl dimethyl carboxymethyl betaine,
lauryl dimethyl alpha-carboxyethyl betaine,
cetyl dimethyl carboxymethyl betaine,
lauryl bis-(2-hydroxyethyl)carboxymethyl betaine,
stearyl bis-(2-hydroxypropyl)carboxymethyl betaine,
oleyl dimethyl gamma-carboxypropyl betaine,
lauryl bis-(2-hydroxypropyl)alpha-carboxyethyl betaine, etc.

The sulfobetaines may be represented by:
coco dimethyl sulfopropyl betaine,
stearyl dimethyl sulfopropyl betaine,
lauryl dimethyl sulfoethyl betaine,
lauryl bis-(2-hydroxyethyl)sulfopropyl betaine and the like. Amido betaines and amidosulfo betaines, wherein the $RCONH(CH_2)_3$ radical is attached to the nitrogen atom of the betaine, may also be used.

Other surfactants that may be present in the personal care product include amphoteric surfactants and non-ionic surfactants.

Examples of amphoteric surfactants are derivatives of aliphatic secondary and tertiary amines in which the aliphatic radical is straight chain or branched and wherein one of the aliphatic substituents contains from about 8 to about 18 carbon atoms and one contains an anionic water-solubilizing group, e.g., carboxy, sulfonate, sulfate, phosphate, or phosphonate. Examples of these compounds are sodium 3-dodecylaminopropionate, sodium 3-dodecylaminopropane sulfonate, and N-alkyltaurines such as the reaction product of dodecylamine and sodium isethionate, and N-higher alkyl aspartic acids.

Nonionic surfactants, which are preferably used in combination with an anionic, amphoteric or zwitterionic surfactant, can be broadly defined as compounds produced by the condensation of a hydrophilic alkylene oxide group with an aliphatic or alkyl aromatic hydrophobic compound. Examples of preferred classes of nonionic surfactants are:
1. Long chain tertiary amine oxides corresponding to the following general formula:

wherein $R_1$ contains an alkyl, alkenyl or monohydroxy alkyl radical of from about 8 to about 18 carbon atoms, up to about 10 ethylene oxide moieties, and up to 1 glyceryl moiety, and $R_2$ and $R_3$ contain from 1 to about 3 carbon atoms and up to about 1 hydroxy group, e.g., methyl, ethyl, propyl, hydroxyethyl, or hydroxypropyl radicals. Examples of amine oxides suitable for use in this invention include:
dimethyldodecylamine oxide,
oleyldi(2-hydroxyethyl)amine oxide,
dimethyloctylamine oxide,
dimethyldecylamine oxide,
dimethyltetradecylamine oxide,
3,6,9-trioxaheptadecyldiethylamine oxide,
di(2-hydroxyethyl)tetradecylamine oxide,
2-dodecoxyethyldimethylamine oxide,
3-dodecoxy-2-hydroxypropyldi(3-hydroxypropyl)amine oxide, and
dimethylhexadecylamine oxide.
2. Long chain tertiary phosphine oxides corresponding to the following general formula:

wherein R contains an alkyl, alkenyl or monohydroxyalkyl radical ranging from 8 to 18 carbon atoms in chain length, up to about 10 ethylene oxide moieties, and up to 1 glyceryl moiety and R' and R" are each alkyl or monohydroxyalkyl groups containing from 1 to 3 carbon atoms. Examples of suitable phosphine oxides are:
dodecyldimethylphosphine oxide,
tetradecyldimethylphosphine oxide, tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropylphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide, and
2-hydroxydodecyldimethylphosphine oxide.

3. Long chain dialkyl sulfoxides containing one short chain alkyl or hydroxy alkyl radical of 1 to about 3 carbon atoms (usually methyl) and one long hydrophobic chain which contains alkyl; alkenyl, hydroxy alkyl, or keto alkyl radicals containing from about 8 to about 20 carbon atoms, up to about 10 ethylene oxide moieties, and up to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

In addition to surfactants, in one embodiment, the personal care product may contain a polyol such as glycerin, propylene glycol, sorbitol, or other cosmetically acceptable glycols. One or more polyols may be present in the personal care product in an amount generally from about 0.5% to about 10% by weight, such as from about 2% to about 5% by weight.

In one embodiment, the personal care product may also contain a fatty ester. Fatty esters include glycerides, such as mono-, di-, and tri-glycerides. The glycerides may comprise esters of glycerol and long chain carboxylic acids, such as $C_{12}$ to $C_{22}$ carboxylic acids. These types of materials can be obtained from vegetable and animal fats and oils such as castor oil, safflower oil, cottonseed oil, corn oil, olive oil, cod liver oil, almond oil, avocado oil, palm oil, sesame oil, lanolin and soybean oil. Particular triglycerides that may be used include caprylic/capric triglyceride. One or more fatty acid esters may be present in the personal care product in an amount from about 0.5% to about 15% by weight, such as from about 5% to about 12% by weight.

In still another embodiment, the personal care product may contain a non-volatile silicone. The silicone may comprise a polyalkyl siloxane, a polyaryl siloxane, a polyalkyl aryl siloxane or a polyether siloxane copolymer. The silicone can be present in the composition in an amount from about 0.1% to about 10% by weight, such as in an amount from about 0.5% to about 5% by weight.

The composition can contain one or more preservatives including dimethylolhydantoin, benzyl alcohol, methylparaben, propylparaben, and imidazolidinyl urea. One or more preservatives can be present in the personal care product in an amount from about 0.1% to about 5% by weight, such as in an amount from about 0.5% to about 2% by weight.

The viscosity building composition of the present disclosure may be used with various different types of actives or benefit agents when contained in a product. The viscosity building properties of the composition, for instance, may allow for the actives or benefit agents to remain uniformly mixed within the product which may increase efficacy. Examples of actives that may be used in conjunction with the viscosity building composition include depigmentation agents; reflectants; detangling/wet combing agents; film forming polymers; humectants; amino acid agents; antimicrobial agents; allergy inhibitors; anti-acne agents; anti-aging agents; anti-wrinkling agents, antiseptics; analgesics; antitussives; antipruritics; local anesthetics; anti-hair loss agents; hair growth promoting agents; hair growth inhibitor agents, anti-dandruff agents, antihistamines; antiinfectives; inflammation inhibitors; anti-emetics; anticholinergics; vasoconstrictors; vasodilators; wound healing promoters; peptides, polypeptides and proteins; deodorants and antiperspirants; medicament agents; skin emollients and skin moisturizers; vitamins; tanning agents; skin lightening agents; antifungals such as antifungals for foot preparations; depilating agents; shaving preparations; external analgesics; perfumes; counterirritants; hemorrhoidals; insecticides; poison ivy products; poison oak products; burn products; anti-diaper rash agents; prickly heat agents; make-up preparations; vitamins; amino acids and their derivatives; herbal extracts; retinoids; flavoids; sensates; anti-oxidants; secondary hair and/or skin conditioners; pearlescent agents; hair lighteners; chelating agents; cell turnover enhancers; coloring agents; pigments; sunscreens and the like, and mixtures thereof.

Examples of suitable reflectants nonexclusively include mica, alumina, calcium silicate, glycol dioleate, glycol distearate, silica, sodium magnesium fluorosilicate, and mixtures thereof.

Examples of suitable UV absorbers include benzophenone, bornelone, butyl paba, cinnamidopropyl trimethyl ammonium chloride, disodium distyrylbiphenyl disulfonate, paba, potassium methoxycinnamate, and mixtures thereof.

Suitable detangling/wet combing agents nonexclusively include dioleoylamidoethyl hydroxythylmonium methosulfate, di (soyoylethyl) hydroxyethylmonium methosulfate, hydroxyethyl behenamidopropyl dimonium chloride, olealkonium chloride, polyquaternium 47, stearalkonium chloride, tricetylmonium chloride, and mixtures thereof.

Suitable film forming polymers include those that, upon drying, produce a substantially continuous coating or film on the hair, skin, or nails. Nonexclusive examples of suitable film forming polymers include acrylamidopropyl trimonium chloride/acrylamide copolymer; corn starch/acrylamide/sodium acrylate copolymer; polyquaternium 10; polyquaternium 47; polyvinylmethyl/maleic anhydride copolymer; styrene/acrylates copolymers; and mixtures thereof.

Commercially available humectants which are capable of providing moisturization and conditioning properties to the cleansing composition are suitable for use in the present invention. The humectant is preferably present in an amount of from about 0 percent to about 10 percent, more preferably from about 1.5 percent to about 7 percent, and most preferably from about 2 percent to about 5 percent, based on the overall weight of the composition. Examples of suitable humectants nonexclusively include: 1) water soluble liquid polyols selected from the group comprising glycerine, propylene glycol, hexylene glycol, butylene glycol, pentylene glycol, dipropylene glycol, and mixtures thereof; 2) polyalkylene glycol of the formula VI:

$$HO\text{---}(R''O)_b\text{-H} \qquad\qquad VI.$$

wherein R" is an alkylene group having from about 2 to about 4 carbon atoms and b is an integer of from about 1 to about 10, such as PEG 4;

3) polyethylene glycol ether of methyl glucose of formula VII:

$$CH_3\text{-}C_6H_{10}O_5\text{-}(OCH_2CH_2)_c\text{-}OH \qquad \text{VII.}$$

wherein c is an integer from about 5 to about 25;
4) urea; 5) fructose; 6) glucose; 7) honey; 8) lactic acid; 9) maltose; 10) sodium glucuronate; and 11) mixtures thereof.

Suitable amino acid agents include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, capryloyl silk amino acid, caprylol collagen amino acids; capryloyl kertain amino acids; capryloyl pea amino acids; cocodimonium hydroxypropyl silk amino acids; corn gluten amino acids; cysteine; glutamic acid; glycine; hair keratin amino acids; hair amino acids such as aspartic acid, threonine, serine, glutamic acid, proline, glycine, alanine, half-cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof.

Suitable proteins include those polymers that have a long chain, i.e. at least about 10 carbon atoms, and a high molecular weight, i.e. at least about 1000, and are formed by self-condensation of amino acids. Nonexclusive examples of such proteins include collagen, deoxyribonuclease, iodized corn protein; keratin; milk protein; protease; serum protein; silk; sweet almond protein; wheat germ protein; wheat protein; wheat protein, alpha and beta helix of keratin proteins; hair proteins, such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

Examples of suitable vitamins nonexclusively include vitamin B complex; including thiamine, nicotinic acid, biotin, pantothenic acid, choline, riboflavin, vitamin B6, vitamin B12, pyridoxine, inositol, carnitine; vitamins A, C, D, E, K and their derivatives such as vitamin A palmitate and pro-vitamins, e.g. (i.e. panthenol (pro vitamin B5) and panthenol triacetate) and mixtures thereof.

Examples of suitable antibacterial agents nonexclusively include bacitracin, erythromycin, neomycin, tetracycline, chlortetracycline, quaternary ammonium agents such as benzethonium chloride and benzalkonium chloride, phenol, and mixtures thereof.

Examples of suitable skin emollients and skin moisturizers nonexclusively include mineral oil, lanolin, vegetable oils, isostearyl isostearate, glyceryl laurate, methyl gluceth 10, methyl gluceth 20 chitosan, and mixtures thereof.

Examples of suitable secondary hair conditioners nonexclusively volatile silicones. When used, the volatile silicone conditioning agent preferably has an atmospheric pressure boiling point less than about 220° C. The volatile silicone conditioner is present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof.

Examples of suitable hair moisturizers nonexclusively include panthenyl ethyl ether, phytantriol, and mixtures thereof. Examples of sunscreen agents nonexclusively include butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, padimate o, red petrolatum, and mixtures thereof.

An example of a suitable tanning agent nonexclusively includes dihydroxyacetone.

Examples of skin lightening agents nonexclusively include hydroquinone, catechol and its derivatives, ascorbic acid and its derivatives, and mixtures thereof.

Examples of suitable insecticides (including insect repellents, anti-scabies and anti-lice treatments) nonexclusively include permethrin, pyrethrin, piperonyl butoxide, imidacloprid, N,N-diethyl toluamide, which refers to the material containing predominantly the meta isomer, i.e., N,N-diethyl-m-toluamide, which is also known as DEET; compounds of the formula VIII.

wherein
R5 is a branched or unbranched alkyl group having about 1 to about 6 carbon atoms;
R6 is H, methyl or ethyl;
R7 is a branched or unbranched alkyl or alkoxy group having from about 1 to about 8 carbon atoms; and
K is a —CN or a —COOR8 group, wherein
R8 is a branched or unbranched alkyl group having from about 1 to about 6 carbon atoms,
natural or synthetic pyrethroids, whereby the natural pyrethroids are contained in pyrethrum, the extract of the ground flowers of *Chrysanthemum cinerariaefolium* or *C coccineum*; and mixtures thereof. Within the structure of Formula VIII. are ethyl 3-(N-butylacetamido)propionate, wherein R7 is a CH3 group, R5 is an n-butyl group, R6 is H, K is COOR8 and R8 is ethyl, which is available commercially from Merck KGaA of Darmstadt, Germany under the name, "Insect Repellent 3535."

An example of an anti fungal for foot preparations nonexclusively includes tolnaftate.

Examples of suitable depilating agents nonexclusively include calcium thioglycolate, magnesium thioglycolate, potassium thioglycolate, strontium thioglycolate, and mixtures thereof.

Examples of suitable external analgesics and local anesthetics nonexclusively include benzocaine, dibucaine, benzyl alcohol, camphor, capsaicin, capsicum, capsicum oleoresin, juniper tar, menthol, methyl nicotinate, methyl salicylate, phenol, resorcinol, turpentine oil, and mixtures thereof.

Examples of suitable antiperspirants and deodorants nonexclusively include aluminium chlorohydrates, aluminium zirconium chlorohydrates, and mixtures thereof.

Examples of suitable counterirritants nonexclusively include camphor, menthol, methyl salicylate, peppermint and clove oils, ichtammol, and mixtures thereof.

An example of a suitable inflammation inhibitor nonexclusively includes hydrocortisone.

Examples of suitable hemorrhoidal products nonexclusively include the anesthetics such as benzocaine, pramoxine hydrochloride, and mixtures thereof; antiseptics such as benzethonium chloride; astringents such as zinc oxide, bismuth subgallate, balsam Peru, and mixtures thereof; skin protectants such as cod liver oil, vegetable oil, and mixtures thereof.

As used herein, "hair loss treatment agents" shall include agents capable of growing hair and/or agents capable of preventing the loss of hair. By "effective amount," it is meant an amount effective for treating hair loss and may range from, based upon the total weight of the cleansing composition, from about 0.001 percent to about 20 percent, e.g., preferably from about 1 percent to about 5 percent. Examples of benefit agents suitable for treating hair loss include, but are not limited to potassium channel openers or peripheral vasodilators such as minoxidil, diazoxide, and compounds such as N*-cyano-N-(tert-pentyl)-N-3-pyridinyl-guanidine ("P-1075") as disclosed in U.S. Pat. No. 5,244,664, which is incorporated herein by reference; vitamins, such as vitamin E and vitamin C, and derivatives thereof such as vitamin E acetate and vitamin C palmitate; hormones, such as erythropoietin, prostaglandins, such as prostaglandin EI and prostaglandin F2-alpha; fatty acids, such as oleic acid; diruretics such as spironolactone; heat shock proteins ('HSP"), such as HSP 27 and HSP 72; calcium channel blockers, such as verapamil HCL, nifedipine, and diltiazemamiloride; immunosuppressant drugs, such as cyclosporin and Fk-506; 5 alpha-reductase inhibitors such as finasteride; growth factors such as, EGF, IGF and FGF; transforming growth factor beta; tumor necrosis factor; non-steroidal anti-inflammatory agents such as benoxaprofen; retinoids such as tretinoin; cytokines, such as IL-6, IL-1 alpha, and IL-1 beta; cell adhesion molecules such as ICAM; glucorcorticoids such as betametasone; botanical extracts such as aloe, clove, ginseng, rehmannia, swertia, sweet orange, zanthoxylum, *Serenoa repens* (saw palmetto), *Hypoxis rooperi*, stinging nettle, pumpkin seeds, and rye pollen; other botanical extracts including sandlewood, red beet root, *chrysanthemum*, rosemary, burdock root and other hair growth promoter activators which are disclosed in DE 4330597 which is incorporated by reference in its entirety herein; homeopathic agents such as Kalium Phosphoricum D2, Azadirachta indica D2, and Joborandi DI; genes for cytokines, growth factors, and male-pattered baldness; antifungals such as ketoconazole and elubiol; antibiotics such as streptomycin; proteins inhibitors such as cycloheximide; acetazolamide; benoxaprofen; cortisone; diltiazem; hexachlorobenzene; hydantoin; nifedipine; penicillamine; phenothaiazines; pinacidil; psoralens, verapamil; zidovudine; alpha-glucosylated rutin having at least one of the following rutins: quercetin, isoquercitrin, hespeddin, naringin, and methylhesperidin, and flavonoids and transglycosidated derivatives thereof which are all disclosed in JP 7002677, which is incorporated by reference in its entirety herein; and mixtures thereof.

Examples of benefit agents suitable for use in inhibiting hair growth include: serine proteases such as trypsin; vitamins such as alpha-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin: glucocorticoids such as betamethasone, and dexamethosone; antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin, gold salts; hydantoins; ibuprofen; imipramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof. The composition may contain, based upon the total weight of the composition, from about 0.001 percent to about 20 percent, e.g. from about 0.01 percent to about 5 percent, of a hair growth inhibiting agent.

Examples of suitable anti-aging agents include, but are not limited to inorganic sunscreens such as titanium dioxide and zinc oxide; organic sunscreens such as octyl-methyl cinnamates and derivatives thereof; retinoids; vitamins such as vitamin E, vitamin A, vitamin C, vitamin B, and derivatives thereof such as vitamin E acetate, vitamin C palmitate, and the like; antioxidants including beta carotene, alpha hydroxy acid such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucopehtonic acid, glucopheptono 1,4-lactone, gluconic acid, gluconolactone, glucuronic acid, glucurronolactone, glycolic acid, isopropyl pyruvate, methyl pyruvate, mucic acid, pyruvia acid, saccharic acid, saccaric acid 1,4-lactone, tartaric acid, and tartronic acid; beta hydroxy acids such as beta-hydroxybutyric acid, beta-phenyl-lactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, safflower, and mixtures thereof. Suitable amounts of anti-aging agents include, based upon the total weight of the cleansing composition, from about 0.01 percent to about 10 percent, e.g. from about 0.04 percent to about 5 percent.

Examples of suitable anti-acne agents include, but are not limited to topical retinoids (tretinoin, isotretinoin, motretinide, adapalene, tazarotene, azelaic acid, retinol); salicylic acid; benzoyl peroxide; resorcinol; antibiotics such as tetracycline and isomers thereof, erythromycin, and the anti-inflammatory agents such as ibuprofen, naproxen, hetprofen; botanical extracts such as alnus, arnica, artemisia capillaris, asiasarum root, birth, calendula, chamomile, cnidium, comfrey, fennel, galla rhois, hawthrom, houttuynia, hypericum, jujube, kiwi, licorice, magnolia, olive, peppermint, philodendron, salvia, sasa albo-marginata; imidazoles such as ketoconazole and elubiol, and those described in Gollnick, H et al. 196(I) Dermatology Sebaceous Glands, Acne and Related Disorders, 119-157 (1998), which is incorporated by reference herein, and mixtures thereof. Suitable amount of anti-acne agents may be present in an amount, based upon the total weight of the cleansing composition, from about 0.01 percent to about 10 percent, e.g. from about 0.04 percent to about 5 percent.

Suitable effective amounts of depigmentation agents include, based upon the total weight of the cleansing composition, from about 0.01 percent to about 10 percent, e.g. from about 0.04 percent to about 5 percent. Examples of suitable depigmentation agents include, but are not limited to retinoids such as retinol; Kojic acid and its derivatives such as, for example, kojic dipalmitate; hydroquinone and it derivatives such as arbutin; transexamic acid; vitamins such as niacin, vitamin C and its derivatives; azelaic acid; placertia; licorice; extracts such as chamomile and green tea, and mixtures thereof.

As used herein, "dandruff treatment agent," "seborrheic dermatitis treatment agent," or a "psoriasis treatment agent," respectively, shall include agents capable of treating the symptoms and/or the diseases of dandruff, seborrheic dermatitis, and psoriasis, respectively. By "effective amount," it is meant an amount effective for treating the disease and/or the symptoms associated therewith and preferably may range from, based upon the total weight of the cleansing composition, from about 0.001 percent to about 10 percent, e.g. from about 0.01 percent to about 5 percent. Examples of agents effective in the treatment of dandruff, seborrheic dermatitis, and psoriasis as well as the symptoms associated therewith include, but are not limited to, zinc pyrithione, shale oil and derivatives thereof such as sulfonated shale oil, selenium sulfide, sulfur; salicylic acid; coal tar; povidoneiodine, imidazoles such as ketoconazole, dichlorophenyl imidazolodioxalan, which is commercially available from Janssen Pharmaceutica, N.V., under the tradename, "Elubiol", clotrimazole, itraconazole, miconazole, climbazole, tioconazole, sulconazole, butoconazole, fluconazole, miconazolenitrite and any possible stereo isomers and derivatives thereof such as anthralin; piroctone olamine (Octopirox); selenium sulfide; ciclopirox olamine; anti-psoriasis agents such as vitamin D analogs, e.g. calcipotriol, calcitriol, and tacaleitrol; vitamin A analogs such as esters of vitamin A, e.g. vitamin A palmitate, retinoids, retinols, and retinoic acid; corticosteroids such as hydrocortisone, clobetasone, butyrate, clobetasol propionate and mixtures thereof.

In one embodiment, the personal care product comprises a shampoo, such as an anti-dandruff shampoo or a body wash. For instance, the viscosity building composition of the present disclosure has been found to work particularly well with a pyrithione. As used herein, a pyrithione comprises a pyrithione, a polyvalent metal salt of pyrithione, a pyrithione complex, and the like. For instance, the pyrithione may comprise a zinc salt or a sodium salt of pyrithione. The viscosity building composition of the present disclosure has been found to be well suited to maintaining the pyrithione evenly distributed throughout the product. The pyrithione may be present in the personal care product in an amount from about 0.01% to about 5% by weight, such as from about 0.1% to about 2% by weight.

The personal care product may also contain a liquid carrier. In general, any suitable liquid carrier may be used that does not interfere with the intended function of the product. The liquid carrier, for instance, may comprise water, an alcohol, or mixtures thereof. The liquid carrier may be present in the personal care product in an amount from about 10% to about 95% by weight, such as in an amount from about 40% to about 80% by weight.

The present disclosure may be better understood with reference to the following example.

Example No. 1

The following compositions were formulated in order to demonstrate some of the benefits and advantages of the present disclosure.

Skin base formulations of (1) 3% glycerin, 0.25% Xanthan gum, 7.5% caprylic/capric triglyceride ("CCT") and 7.5% shea butter or (2) 9% dicaprylyl carbonate (LONZEST DC) and 6% Jojoba oil, with 0.75% phenoxyethanol, chlorphenesin, and caprylyl glycol blend (Mikrokill™ COS), and either 1.5 or 3% of cetyl stearyl alcohol, and either 1 or 2% emulsifier combination were prepared.

Table 1 shows the hydrophilic-lipophilic balance values (HLB) of various ratios of emulsifier combinations of polyglyceryl esters.

In Table 1 below, the following designation is used to identify the glyceryl esters:

X—Y—Z wherein X is the number of glyceryl molecules. Y refers to the number of ester groups. For instance, 1 indicates a monoester, 2 indicates a diester, and so forth. Z identifies the fatty acid used to construct the polyglyceryl ester. S stands for stearate, and O stands for oleate. As shown below, by changing the weight ratio of the monoester to the polyester can significantly change the HLB number. In one embodiment, the polyglyceryl esters can be formulated so as to have an HLB number that substantially matches the HLB number of one or more components in a product, such as the oil phase of a product.

TABLE 1

| Ratio | 5:95 | 10:90 | 20:80 | 30:70 | 40:60 | 50:50 | 60:40 | 70:30 | 80:20 | 90:10 | 95:5 |
|---|---|---|---|---|---|---|---|---|---|---|---|
| 10-1-S: 6-2-S | 6.0 | 6.3 | 6.6 | 6.9 | 7.2 | 7.5 | 7.8 | 8.1 | 8.4 | 8.7 | 8.9 |
| 10-1-S: 3-1-S | 6.0 | 6.3 | 6.6 | 6.9 | 7.2 | 7.5 | 7.8 | 8.1 | 8.4 | 8.7 | 8.9 |
| 10-1-O: 6-2-S | 6.3 | 6.6 | 7.2 | 7.8 | 8.4 | 9.0 | 9.6 | 10.2 | 10.8 | 11.4 | 12.0 |
| 10-1-O: 3-1-S | 6.3 | 6.6 | 7.2 | 7.8 | 8.4 | 9.0 | 9.6 | 10.2 | 10.8 | 11.4 | 12.0 |

In a first set of experiments, various different emulsifier combinations were tested that had an HLB of 6. The HLB 6 emulsifier combinations used in the test skin base formulations, seen in Table 2 included either 5 parts polyglyceryl-10-stearate (Polyaldo™ 10-1-S) and 95 parts polyglyceryl-6-distearate (Polyaldo™ HGDS KFG (6-2-S)); 5 parts polyglyceryl-10 oleate (Polyaldo™ 10-1-0 KFG (NON GMO)) and 95 parts polyglyceryl-6-distearate (Polyaldo™ HGDS KFG (6-2-S)); or 90 parts polyethylene glycol (2) stearyl ether (steareth-2) and 10 parts polyethylene glycol (21) stearyl ether (steareth-21). The above POLYALDO products are commercially available from Lonza, Inc.

Viscosity measurements were taken for each formulation using a RVT dial viscometer with a T-D spindle at 4 rpm. Samples were stored in 60 ml glass jars at 25° C. in an incubator and removed from the incubator and placed in a water bath at 25° C. for at least two hours prior to viscosity measurement. After assembly of the viscometer without the guard shaft, the T-D spindle was lowered into the jar and centered in the test formulation; measurements were recorded at 1 minute, and the spindle was cleaned after each measurement.

Figure 1:
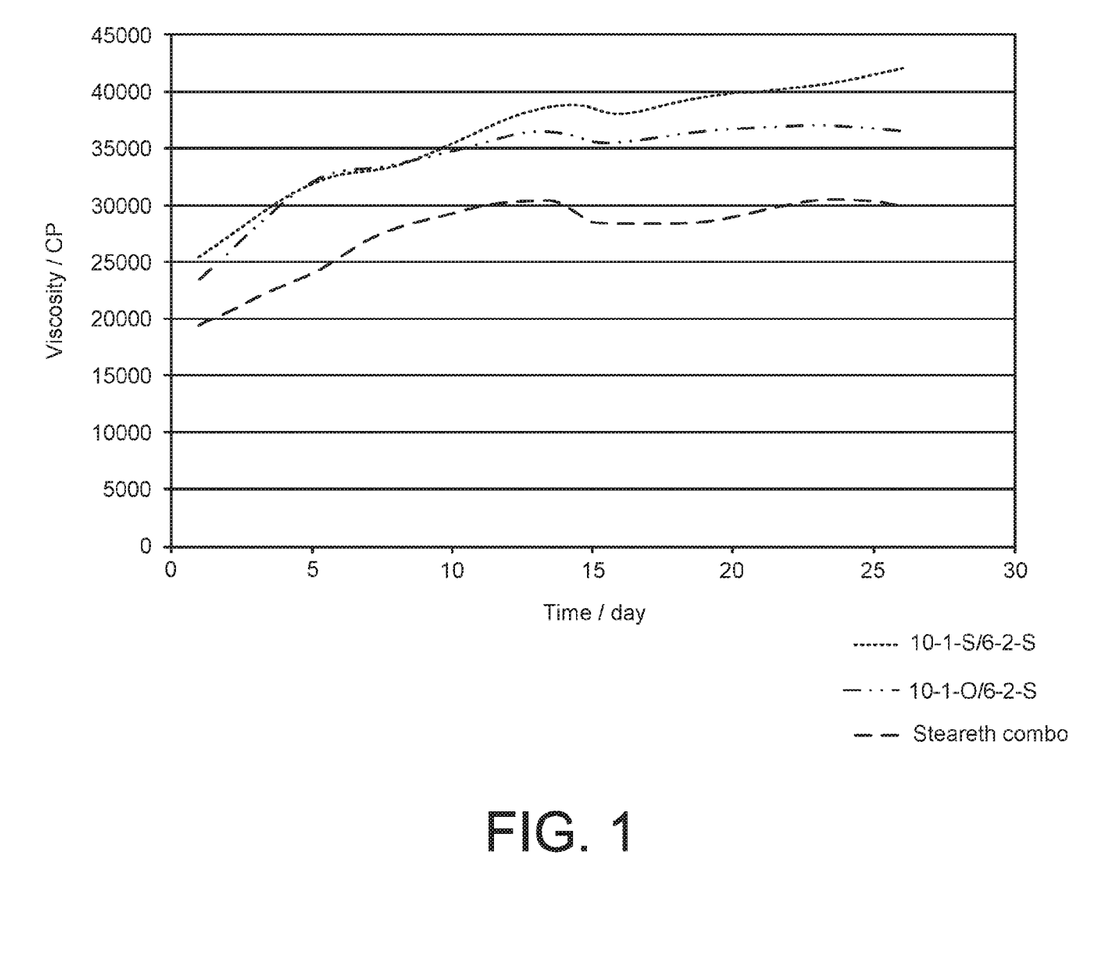
FIGS. 1, 2, 3, and 4 are graphical representations of some of the results obtained in the examples described below.

Table 2 demonstrates the viscosity of skin base formulations containing 3% cetearyl alcohol and 2% HLB 6 emulsifier combination. As illustrated in FIG. 1, both Polyaldo™ emulsifiers yield significantly higher viscosity emulsions in comparison to the combination of Steareth 2/Steareth 21, a conventional emulsifier.

TABLE 2

Viscosity of skin base formulations (3% Cetearyl Alcohol, 2% Emulsifier blend)

| Time (Days) | 10-1-S/6-2-S (5:95) | 10-1-O/6-2-S (5:95) | Steareth Mix (90:10) |
|---|---|---|---|
| 1 | 25500 | 23500 | 19500 |
| 5 | 32000 | 32000 | 24000 |
| 8 | 33500 | 33500 | 28000 |
| 13 | 38500 | 36500 | 30500 |
| 15 | 38500 | 35500 | 28500 |
| 16 | 38000 | 35500 | 28500 |
| 19 | 39500 | 36500 | 28500 |
| 23 | 40500 | 37000 | 30500 |
| 26 | 42000 | 36500 | 30000 |

Figure 2:
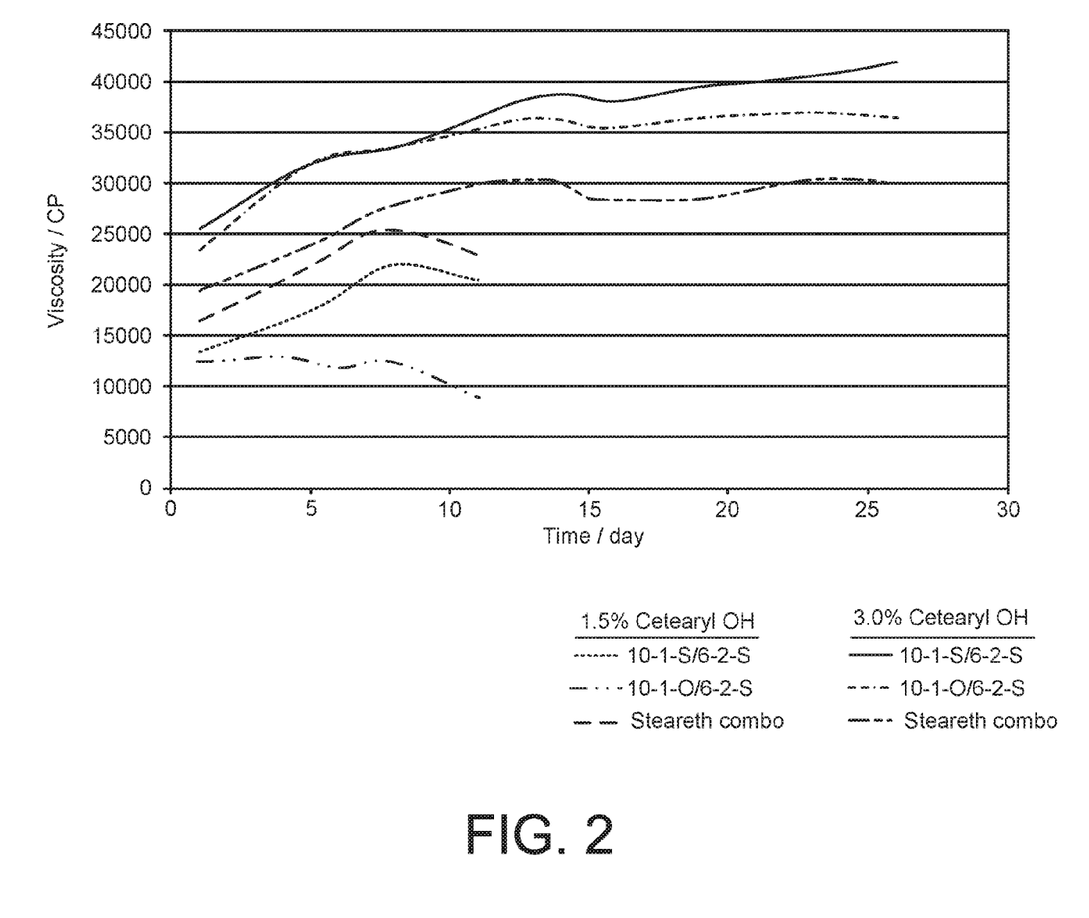

Table 3 contains viscosity measurements for skin base formulations with 2% emulsifier and 1.5% cetearyl alcohol. FIG. 2 illustrates the effect of varying fatty alcohol loads on the viscosity measurements for the formulations. As FIG. 2 reveals, all of the emulsifier combinations with the higher (3%) fatty alcohol content demonstrate increased viscosity in comparison to the emulsifier combinations with the lower (1.5%) fatty alcohol content. Thus, Polyaldo™ emulsifiers demonstrate synergistic viscosity build with increasing amounts of fatty alcohols.

TABLE 3

Viscosity of skin base formulations (3% Cetearyl Alcohol, 2% Emulsifier blend)

| Time (Days) | 10-1-S/6-2-S (5:95) | 10-1-O/6-2-S (5:95) | Steareth Mix (90:10) |
|---|---|---|---|
| 1 | 13500 | 12500 | 16500 |
| 4 | 16500 | 13000 | 20500 |
| 6 | 19000 | 12000 | 23500 |
| 8 | 22000 | 12500 | 25500 |
| 11 | 20500 | 9000 | 23000 |

Figure 3:
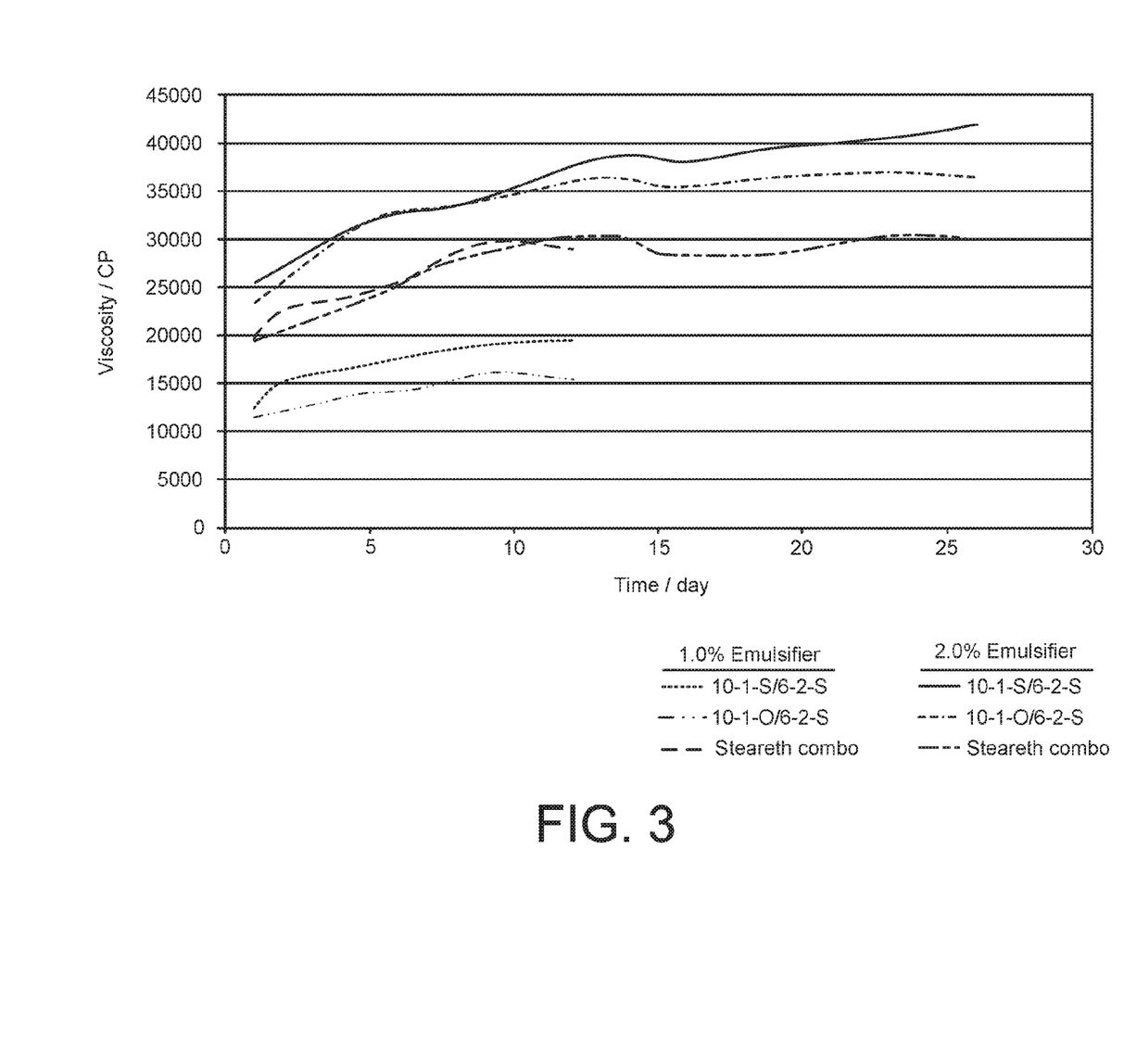

Table 4 shows the viscosities of skin base formulations with 1% emulsifier and 3% cetearyl alcohol. FIG. 3 illustrates the effect of varying emulsifier load on the viscosity measurements for the formulations. As shown in FIG. 3, lowering the amount of Polyaldo™ emulsifier in the base formulation leads to decreased viscosity. The base formulation with Steareth 2/Steareth 21 emulsifier was relatively unaffected by a lowered emulsifier load.

TABLE 4

Viscosity of skin base formulations (3% Cetearyl Alcohol, 1% Emulsifier blend)

| Time (Days) | 10-1-S/6-2-S (5:95) | 10-1-O/6-2-S (5:95) | Steareth Mix (90:10) |
|---|---|---|---|
| 1 | 12500 | 11500 | 19500 |
| 2 | 15000 | 12000 | 22500 |
| 5 | 17000 | 14000 | 24500 |
| 7 | 18000 | 14500 | 26500 |
| 9 | 19000 | 16000 | 29500 |
| 12 | 19500 | 15500 | 29000 |

Figure 4:
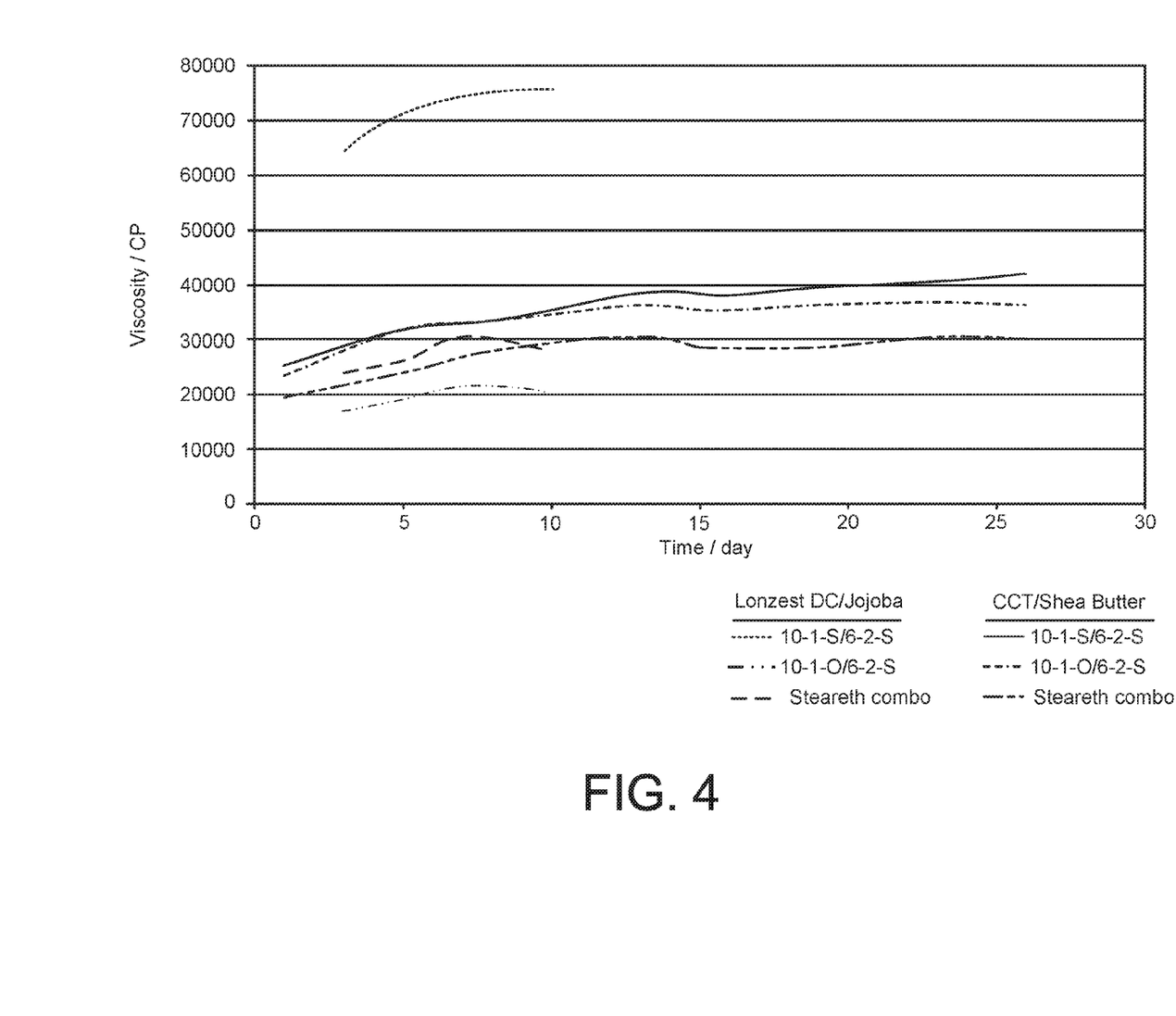

Table 5 shows the viscosities of skin base formulations with an oil phase of 9% dicaprylyl carbonate and 6% Jojoba oil. FIG. 4 illustrates the effect of varying oil phase and HLB on the viscosity measurements for the formulations. In FIG. 4, the CCT/Shea Butter viscosities reflect the formulations in Table 2 and FIG. 1. The viscosities for the dicaprylyl carbonate Jojoba formulation reflect formulations whose emulsifier ratios have been adjusted to match the HLB of the new oil phase; the introduction of the new oil phase required a shift for 10-1-O/6-2-S from a 90:10 ratio to a 50:50 ratio. As a result of the adjusted emulsifier ratio, the resulting emulsifier blend contained greater amounts of a polyglyceryl ester made from an unsaturated fatty acid (oleate) which reduced the viscosity of the blend. The combination of the polyglyceryl monostearate and the polyglyceryl distearate, however, unexpectedly and dramatically increased the viscosity of the formulation in comparison to the other emulsifier blends. This result was achieved when using greater amounts of the monostearate than the distearate (90:10 ratio).

TABLE 5

Viscosity of skin base formulations (9% Lonzest DC, 6% Jojoba Oil, 3% Cetearyl Alcohol, 1 or 3% Emulsifier)

| Time (Days) | 10-1-S/6-2-S (90:10) | 10-1-O/6-2-S (50:50) | Steareth Mix (90:10) |
|---|---|---|---|
| 3 | 64500 | 17000 | 24000 |
| 5 | 71500 | 19000 | 26000 |
| 7 | 74500 | 21500 | 30500 |
| 10 | 76000 | 20500 | 28000 |

Example No. 2

For exemplary purposes only, below are embodiments of personal care products that can be made in accordance with the present disclosure. The below products represent body washes that contain a pyrithione as an active agent.

The body wash formulations are as follows:

TABLE 6

| Ingredient | Chemical Name | Source | Formulation No. 1 | Formulation No. 2 |
|---|---|---|---|---|
| Water | Water | — | q.s to 100 | q.s to 100 |
| Viscolam CK-1 | Acrylates Copolymer | Lamberti | 3.00 | 3.00 |
| Standapol WAQ-LC | Sodium Lauryl Sulfate | BASF | 10.00 | 10.00 |
| Steol CS 270 | Sodium Laureth Sulfate | Stepan | 20.00 | 20.00 |

TABLE 6-continued

| Ingredient | Chemical Name | Source | Formulation No. 1 | Formulation No. 2 |
|---|---|---|---|---|
| Lauramide MEA | Lauramide MEA | — | 2.65 | 2.65 |
| Polyaldo 6-2-S | Polyglyceryl-6 Distearate | Lonza Consumer Care | 1.00 | 1.00 |
| Cetearyl Alcohol | Cetearyl Alcohol | — | 0.50 | 0.50 |
| Zinc Omadine ™ (48%) FPS | Zinc Pyrithione | Lonza Consumer Care | | 0.522 |
| Zinc Omadine ™ Enhanced CP Dispersion | Zinc Pyrithione | Lonza Consumer Care | 0.522 | — |
| Mikrokill COS | Phenoxyethnol & Caprylyl Glycol & Chlorphenesin | Lonza Consumer Care | 0.75 | 0.75 |
| Sodium Chloride | Sodium Chloride | — | 1.00 | 1.00 |
| Citric Acid 10% | Citric Acid | — | q.s | q.s |
| Sodium Hydroxide 10% | Sodium Hydroxide | — | q.s | q.s |
| | | Total | 100.00 | 100.00 |

As shown above, the body wash formulations contain a fatty alcohol in combination with a single type of polyglyceryl ester, namely a polyglyceryl diester. Of particular advantage, the presence of the single polyglyceryl ester minimizes the amount of fatty alcohol necessary for the body wash product to have desired viscosity and other related properties. In particular, the fatty alcohol is present in relation to the polyglyceryl ester at a weight ratio of from 1:2. In addition, the fatty alcohol is present in the product in an amount less than 1% by weight, namely 0.5% by weight.

Example No. 3

For exemplary purposes only, the following are further body wash formulations made in accordance with the present disclosure:

TABLE 7

| Ingredient | Chemical Name | Source | Formulation No. 1 | Formulation No. 2 |
|---|---|---|---|---|
| Water | Water | — | q.s to 100 | q.s to 100 |
| Viscolam CK-1 | Acrylates Copolymer | Lamberti | 3.00 | 3.00 |
| Standapol WAQ-LC | Sodium Lauryl Sulfate | BASF | 10.00 | 10.00 |
| Steol CS 270 | Sodium Laureth Sulfate | Stepan | 20.00 | 20.00 |
| Lauramide MEA | Lauramide MEA | — | 2.65 | 2.65 |
| Polyaldo 10-1-O | Polyglyceryl-10 Oleate | Lonza Consumer Care | 0.25 | 0.25 |
| Polyaldo 6-2-S | Polyglyceryl-6 Distearate | Lonza Consumer Care | 1.00 | 1.00 |
| Cetearyl Alcohol | Cetearyl Alcohol | — | 0.50 | 0.50 |
| Zinc Omadine ™ (48%) FPS | Zinc Pyrithione | Lonza Consumer Care | | 0.522 |
| Zinc Omadine ™ Enhanced CP Dispersion | Zinc Pyrithione | Lonza Consumer Care | 0.522 | — |
| Mikrokill COS | Phenoxyethnol & Caprylyl Glycol & Chlorphenesin | Lonza Consumer Care | 0.75 | 0.75 |
| Sodium Chloride | Sodium Chloride | — | 1.00 | 1.00 |
| Citric Acid 10% | Citric Acid | — | q.s | q.s |
| Sodium Hydroxide 10% | Sodium Hydroxide | — | q.s | q.s |
| | | Total | 100.00 | 100.00 |

As shown above, the above body wash formulations contain a mixture of polyglyceryl esters, namely a polyglyceryl monoester combined with a polyglyceryl diester.

Example No. 4

The following compositions were formulated to further demonstrate some of the benefits and advantages of the present disclosure.

In a first set of experiments, basic formulations of 3% glycerin, 0.25% Xanthan gum, 2% emulsifier combination, 7.5% caprylic/capric triglyceride ("CCT"), 7.5% shea butter, 0.75% phenoxyethanol, chlorphenesin, and caprylyl glycol blend (Mikrokill™ COS), and 3% of cetyl stearyl alcohol were prepared.

As in Example 1, the emulsifier combinations used in the test skin base formulations included either Polyaldo™ 10-1-S, 6-2-S, 10-1-O, steareth-2, or steareth-21. The following designation is used to identify the glyceryl esters:

X—Y—Z wherein X is the number of glyceryl molecules. Y refers to the number of ester groups. For instance, 1 indicates a monoester, 2 indicates a diester, and so forth. Z identifies the fatty acid used to construct the polyglyceryl ester. S stands for stearate, and O stands for oleate.

Viscosity measurements were taken for each formulation using a RVT dial viscometer with a T-D spindle at 4 rpm. Samples were stored in 60 ml glass jars at 25° C. in an incubator for two weeks. The samples were then subsequently removed from the incubator and placed in a water bath at 25° C. for at least two hours prior to viscosity measurement. The measurements were taken as described in Example 1.

Table 8 demonstrates the viscosity of the skin base formulations. The formulations containing polyglyceryl monostearate and the polyglyceryl distearate and the formulations containing multiple polyglyceryl distearates experienced a unexpected and dramatic increase in the viscosity of the formulations in comparison to the other emulsifier blends.

TABLE 8

Viscosity of skin base formulations (7.5% CCT, 7.5% Shea Butter, and 3% Cetearyl Alcohol)

| Emulsifier Combination | HLB | Viscosity |
| --- | --- | --- |
| 6-2-S | 6.0 | 36500 |
| 10-1-S/6-2-S (5/95)* | 6.15 | 42000 |
| 10-1-S/6-2-S (5/95) | 6.15 | 38500 |
| 10-1-S/6-2-S (1/5) | 6.5 | 45000 |
| 10-1-S/6-2-S (2/3) | 7.2 | 38000 |
| 10-1-S/6-2-S (2/1) | 8 | 58000 |
| 10-1-S/6-2-S (4/1) | 8.4 | 44000 |
| 10-1-S | 9.0 | 40000 |
| 10-2-P/6-2-S (5/95) | 6.25 | 43500 |
| 10-2-P/6-2-S (1/9) | 6.5 | 45000 |
| 10-2-P/6-2-S (1/3) | 7.25 | 45000 |
| 10-1-O/6-2-S (5/95) | 6.3 | 38000 |
| 10-1-O/6-2-S (5/95) | 6.3 | 38000 |
| Steareth 2/Steareth 21 (9/1) | 6.0 | 32000 |
| Steareth 2/Steareth 21 (9/1) | 6.0 | 33000 |
| Steareth 2/Seareth 21 (9/1) | 6.0 | 39000 |
| Steareth 2/Steareth 21 (7/3) | 8.0 | 31500 |
| 10-1-S/3-1-S (5/95) | 6.15 | 26500 |

TABLE 8-continued

Viscosity of skin base formulations (7.5% CCT, 7.5% Shea Butter, and 3% Cetearyl Alcohol)

| Emulsifier Combination | HLB | Viscosity |
| --- | --- | --- |
| 10-2-P/3-1-S (5/95) | 6.25 | 28000 |
| 10-1-S/10-10-O (3/2) | 6.6 | 36500 |
| 10-2-P/10-10-O (7/9) | 6.5 | 30000 |
| 10-1-O/10-10-O (2/3) | 6.6 | 8000 |

*(X/Y) indicates ratio of the emulsifier combination.
*HLB 6.0 if not considering the contribution from fatty alcohol, HLB 8.0 if considering fatty alcohol In a second set of experiments, basic formulations of 3% glycerin, 0.25% Xanthan gum, 2% emulsifier combination, 9% Lonzest DC, 6% Jojoba oil, 0.75% phenoxyethanol, chlorphenesin, and caprylyl glycol blend (Mikrokill™ COS), and 3% of cetyl stearyl alcohol were prepared.

Viscosity measurements were taken for each formulation. Table 9 demonstrates the viscosity of the skin base formulations.

TABLE 9

Viscosity of skin base formulations (9% LONZEST DC, 6% Jojoba Oil, and 3% Cetearyl Alcohol)

| Emulsifier Combination | HLB | Viscosity |
| --- | --- | --- |
| 10-1-S/6-2-S (9/1) | 8.7 | 76000 |
| 10-1-O/6-2-S (1/1) | 9.0 | 27000 |
| Steareth 2/Steareth 21 (6/4) | 9.0 | 36000 |
| 10-1-S/10-2-P (1/1) | 10.0 | 43000 |
| Steareth 2/Steareth 21 (1/1) | 10.0 | 31500 |

*HLB 9.0 if not considering the contribution from fatty alcohol, HLB 10.1 if considering fatty alcohol These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims

What is claimed:

1. A viscosity building composition comprising:
   a fatty alcohol;
   a polyglyceryl monoester of a fatty acid; and
   a polyglyceryl polyester of a fatty acid,
   wherein the weight ratio of the polyglyceryl monoester of a fatty acid to the polyglyceryl polyester of a fatty acid in the composition is from about 1:100 to about 100:1, and
   wherein the weight ratio of the fatty alcohol to all of the polyglyceryl esters is from about 1:10 to about 10:1.

2. A viscosity building composition as defined in claim 1, wherein the weight ratio of the polyglyceryl monoester of a fatty acid to the polyglyceryl polyester of a fatty acid is from about 1:50 to about 1:1.

3. A viscosity building composition as defined in claim 1, wherein the polyglyceryl monoester of a fatty acid and the polyglyceryl polyester of a fatty acid are polyglyceryl esters of fatty acids having a carbon chain length of from about 6 carbon atoms to about 26 carbon atoms.

4. A viscosity building composition as defined in claim 1, wherein the polyglyceryl monoester of a fatty acid to the polyglyceryl polyester of a fatty acid each contain from about 2 to about 12 molecules of glycerol per compound.

5. A viscosity building composition as defined in claim 1, wherein the polyglyceryl monoester of a fatty acid comprises polyglyceryl monostearate, polyglyceryl monodecaoleate, polyglyceryl monooleate, and mixtures thereof.

6. A viscosity building composition as defined in claim 1, wherein the fatty alcohol comprises cetyl alcohol, stearyl alcohol, lauryl alcohol, myristyl alcohol, behenyl alcohol, or mixtures thereof.

7. A personal care product containing the viscosity building composition as defined in claim 1.

8. A personal care product as defined in claim 7, wherein the personal care product contains an emollient, a humectant, and at least one surfactant.

9. A personal care product as defined in claim 8, wherein the product contains the fatty alcohol in an amount less than about 5% by weight, and wherein the polyglyceryl monoester of a fatty acid and the polyglyceryl polyester of a fatty acid are both contained in the product in an amount greater than about 0.5% by weight, and in an amount less than about 10% by weight.

10. A personal care product as defined in claim 7, wherein the personal care product comprises a shampoo.

11. A personal care product as defined in claim 10, further comprising pyrithione.

\* \* \* \* \*